(12) United States Patent
Liu et al.

(10) Patent No.: US 6,566,524 B2
(45) Date of Patent: May 20, 2003

(54) METHODS FOR SYNTHESIS OF AMINO-TETRAHYDROISOQUINOLINE-SULFONAMIDE HYDROXAMIC ACIDS

(75) Inventors: Song Liu, San Diego, CA (US); William Martin Rennells, Schenectady, NY (US)

(73) Assignee: The Procter & Gamble Co., Cincinatti, OH (US)

( * ) Notice: Subject to any disclaimer, the term of this patent is extended or adjusted under 35 U.S.C. 154(b) by 0 days.

(21) Appl. No.: 10/027,755

(22) Filed: Dec. 21, 2001

(65) Prior Publication Data
US 2002/0058815 A1 May 16, 2002

(51) Int. Cl.[7] .............................................. C07D 217/02

(52) U.S. Cl. ....................................... 546/141; 546/139

(58) Field of Search ................................ 546/141, 139

(56) References Cited

U.S. PATENT DOCUMENTS 5,962,471 A * 10/1999 Schudok ...................... 514/309

OTHER PUBLICATIONS

Thouin et al, Tetrahedron Letters, vol. 41, pp. 457–460, 2000.*

* cited by examiner

Primary Examiner—Zinna Northington Davis
(74) Attorney, Agent, or Firm—David V. Upite; Holly D. Kozlowski

(57) ABSTRACT

Methods of preparing an amino-substituted-tetrahydroisoquinoline-sulfonamide hydroxamic acid include the steps of providing an amino-substituted-tetrahydroisoquinoline-carboxylate attached to a solid support; reacting the ring nitrogen of the amino-tetrahydroisoquinoline-carboxylate with a sulfonyl chloride; and cleaving the intermediate from the solid support to form an amino-tetrahydroisoquinoline-sulfonamide hydroxamic acid.

20 Claims, No Drawings

METHODS FOR SYNTHESIS OF AMINO-TETRAHYDROISOQUINOLINE-SULFONAMIDE HYDROXAMIC ACIDS

FIELD OF INVENTION

The present invention relates to methods of preparing amino-substituted-tetrahydroisoquinoline-sulfonamide hydroxamic acids. More particularly, the invention relates to the solid phase synthesis of substituted amino-tetrahydroisoquinoline-sulfonamide hydroxamic acids using a solid support. The invention also relates to methods of preparing combinatorial libraries of amino-substituted-tetrahydroisoquinoline-sulfonamide hydroxamic acids.

BACKGROUND ART

The amino-substituted-tetrahydroisoquinoline-carboxylates (amino-substituted-TIQ-carboxylates) and related compounds, such as amino-substituted-tetrahydroisoquinoline-sulfonamide hydroxamic acids (amino-substituted-TIQ-sulfonamide hydroxamic acids), are useful in numerous pharmaceutical applications. Such compounds have been useful in treatment of degenerative joint disorders, disorders of the connective tissue, ulcerations, atherosclerosis, stenosis, inflammation, carcinomatosis, anorexia, and septic shock. Thus, it is desirable to generate amino-substituted-TIQ-sulfonamide hydroxamic acids for testing as potential drug candidates. The acceleration of drug discovery has generated growing demands for efficient synthetic methods to produce therapeutic candidates. Preferably the methods are suitable for use in generating combinatorial libraries.

Schudok, U.S. Pat. No. 5,962,471, teach substituted 6- and amino-substituted-tetrahydroisoquinoline-carboxylates suitable for therapy of disorders involving increased activity of matrix-degrading metalloproteinases. Schudok teaches a method of synthesizing substituted amino-substituted-TIQ-3-(N-hydroxy)carboxamides by successively treating substituted amino-substituted-TIQ-carboxylates with ethyl chloroformate, N-methylmorpholine and O-trimethylsilylhydroxylamine. Thouin et al., *Tetrahedron Letters*, 41:457–460 (2000) teach the synthesis of hydroxamic acids by the nucleophilic displacement of carboxylates from oxime resins using hydroxylamine in a methanol:chloroform solution, and disclose hydroxamic acids prepared using proline, phenylalanine and alanine.

There is a need for facile and efficient methods for the synthesis of amino-substituted-TIQ-sulfonamide hydroxamic acids. It is desirable that the methods conveniently produce combinatorial libraries of compounds.

SUMMARY OF THE INVENTION

It is therefore an object of the invention to provide novel methods of preparing amino-substituted-tetrahydroisoquinoline-sulfonamide hydroxamic acids. It is also an object of the invention to provide novel methods of preparing combinatorial libraries of amino-substituted-tetrahydroisoquinoline-sulfonamide hydroxamic acids.

In accordance with one aspect of the invention, there are provided methods of preparing amino-substituted-tetrahydroisoquinoline-sulfonamide hydroxamic acids having the structure:

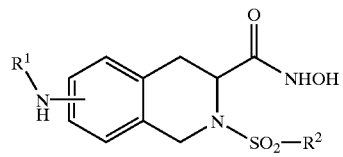

wherein $R^1$ is an alkyl, an aryl, a heterocyclic moiety, an amide, a sulfonamide, a urea, a thiourea, or an alcohol, and $R^2$ is an aryl, a hetero-aromatic ring or a hydrocarbocycle. The methods comprise the steps of providing an orthogonally protected amino-substituted-tetrahydroisoquinoline-carboxylate attached to a solid support; attaching the $R^1$ group to the amino-substituted of the orthogonally protected amino-substituted-tetrahydroisoquinoline-carboxylate; removing the protecting group from the orthogonally protected amino-substituted-tetrahydroisoquinoline-carboxylate to form a deprotected, $R^1$-substituted amino-substituted-tetrahydroisoquinoline-carboxylate, reacting the deprotected, $R^1$-substituted amino-substituted-tetrahydroisoquinoline-carboxylate with a sulfonyl chloride having the structure $R^2SO_2Cl$ to form an intermediate attached to a solid support; and cleaving the intermediate from the solid support to form an amino-substituted-tetrahydroisoquinoline-sulfonamide hydroxamic acid.

In accordance with another aspect of the invention, there are provided methods of preparing amino-substituted-tetrahydroisoquinoline-sulfonamide hydroxamic acids comprising the steps of providing an orthogonally protected amino-substitutent-tetrahydroisoquinoline-carboxylate attached to a solid support; attaching a moiety selected from the group consisting of amides, sulfonamides, ureas, thioureas, alcohols, alkyls and mixtures thereof to the amino-substituent of the orthogonally protected amino-substituted-tetrahydroisoquinoline-carboxylate; removing the protecting group from the orthogonally protected amino-substituted-tetrahydroisoquinoline-carboxylate to form a deprotected amino-substituted-tetrahydroisoquinoline-carboxylate; reacting the amino-substituted-tetrahydroisoquinoline-carboxylate with a sulfonyl chloride to form an intermediate attached to a solid support; and cleaving the intermediate from the solid support to form an amino-substituted-tetrahydroisoquinoline-sulfonamide hydroxamic acid.

In accordance with yet another aspect of the invention, there are provided methods of preparing a combinatorial library of amino-substituted-tetrahydroisoquinoline sulfonamide hydroxamic acids having the structure:

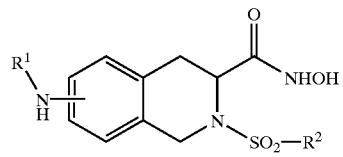

wherein $R^1$ is alkyl, aryl, heterocyclic moiety, amide, sulfonamide, urea, thiourea, or alcohol, and $R^2$ is aryl, hetero-aromatic ring or hydrocarbocycle. The methods comprise the step of providing a support-bound orthogonally protected amino-substituted-tetrahydroisoquinoline-carboxylate. The methods further comprise the steps of attaching a first $R^1$ group to a first portion of the orthogonally protected amino-substituted-tetrahydroisoquinoline-carboxylate and attaching a second $R^1$ group to a second portion of the orthogonally protected amino-substitutedtetrahydroisoquinoline carboxylate, deprotecting the first and second portions of the orthogonally protected amino-substituted-tetrahydroisoquinoline-carboxylate to form first and second deprotected amino-substituted-tetrahydroisoquinoline-carboxylates; attaching a first $R^2$ group to the ring nitrogen of the first deprotected amino-substituted-tetrahydroisoquinoline to form a first support-bound intermediate and attaching a second $R^2$ group to the ring nitrogen of the second deprotected amino-substituted-tetrahydroisoquinoline to form a second support-bound intermediate; and cleaving the first and second support-bound intermediates from the solid support to form first and second amino-substituted-tetrahydroisoquinoline-sulfonamide hydroxamic acids. When the first and second $R^1$ groups are the same, then the first and second $R^2$ groups are different, and when the first and second $R^2$ groups are the same, then the first and second $R^1$ groups are different. The first and second portions of the protected amino-substituted-tetrahydroisoquinoline-carboxylate may be separated prior to attachment of the $R^1$ group, for example by partitioning the orthogonally protected amino-substituted-tetrahydroisoquinoline-carboxylate into at least a first orthogonally protected amino-substituted-tetrahydroisoquinoline-carboxylate and a second orthogonally protected-amino-substituted-tetrahydroisoquinoline-carboxylate.

In accordance with another aspect of the invention, there are provided methods of preparing an amino-substituted-tetrahydroisoquinoline-sulfonamide hydroxamic acid comprising the steps of providing an amino-substituted-tetrahydroisoquinoline intermediate attached to a solid support and having the structure:

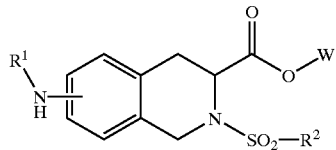

wherein $R^1$ and $R^2$ are defined above, and W represents a solid support; and cleaving the amino-substituted-tetrahydroisoquinoline intermediate from the solid support with a cleaving composition comprising $NH_2ON$ a, $NH_2OH$ and methanol to form an amino-substituted-tetrahydroisoquinoline-sulfonamide hydroxamic acid.

In accordance with yet another aspect of the invention, there are provided methods of preparing amino-substituted-tetrahydroisoquinoline-sulfonamide hydroxamic acid comprising the steps of providing amino-substituted-tetrahydroisoquinoline-carboxylate attached to a solid support; reacting the ring nitrogen of the amino-substituted-tetrahydroisoquinoline-carboxylate with a sulfonyl chloride to form an intermediate; and cleaving the intermediate from the solid support to form an amino-substituted-tetrahydroisoquinoline-sulfonamide hydroxamic acid.

The present invention provides convenient means for producing amino-tetrahydroisoquinoline-sulfonamide hydroxamic acids, and for preparing combinatorial libraries thereof. These and additional objects and advantages will be more fully apparent in view of the following description.

DETAILED DESCRIPTION

As used herein unless specified otherwise, "alkyl" means a hydrocarbon chain which is branched, linear or cyclic, saturated or unsaturated (but not aromatic), substituted or unsubstituted. The term "alkyl" may be used alone or as part of another word where it may be shortened to "alk" (e.g., in alkoxy, alkacyl). Preferred linear alkyl have from one to about twenty carbon atoms, more preferably from one to about ten carbon atoms, more preferably still from one to about six carbon atoms, still more preferably from one to about four carbon atoms; most preferred are methyl or ethyl. Preferred cyclic and branched alkyl have from three to about twenty carbon atoms, more preferably from three to about ten carbon atoms, more preferably still from three to about seven carbon atoms, still more preferably from three to about five carbon atoms. Preferred cyclic alkyl have one hydrocarbon ring, but may have two, three, or more, fused or spirocycle hydrocarbon rings. Preferred alkyl include unsaturated alkyl with from one to about three double or triple bonds, preferably double bonds; more preferably they are mono-unsaturated with one double bond. Also preferred alkyl include saturated alkyl. Saturated alkyl are referred to herein as "alkanyl". Alkyl unsaturated only with one or more double bonds (no triple bonds) are referred to herein as "alkenyl". Alkyl unsaturated with one or more triple bonds are referred to herein as "alkynyl". Preferred substituents of alkyl include halo, alkyl, aryl, heterocycle, hydroxy, alkoxy, aryloxy, thio, alkylthio, arylthio, amino, alkylamino, arylamino, amide, alkylamide, arylamide, formyl, alkacyl, arylacyl, carboxy and its alkyl and aryl esters and amides, sulfo, alkylsulfo, arylsulfo, sulfino, alkylsulfino, arylsulfino, phospho, alkylphospho, arylphospho, phosphino, alkylphosphino, arylphosphino, nitro, and cyano. Substituents of cycloalkyl also include cycloalkyl, aryl and heterocyclic rings which are fused or spirocycle with the initial cycloalkyl. Unsubstituted alkyl are preferred. An alkyl is bonded to another moiety at the "attaching carbon" of the alkyl. As used herein, "primary alkyl" means that the attaching carbon of the alkyl has two or three hydrogens bonded to it; "secondary alkyl" means that the attaching carbon has one hydrogen bonded to it; and "tertiary alkyl" means that the attaching carbon has no hydrogens bonded to it.

As used herein, "heteroatom" means an atom other than carbon, preferably a nitrogen, oxygen, or sulfur atom. As used herein, "alkylene" means an alkyl which connects two other moieties, "heteroalkylene" means an alkylene having one or more heteroatoms in the connecting chain.

As used herein unless specified otherwise, "aryl" means an aromatic hydrocarbon ring (or fused rings) which is substituted or unsubstituted. The term "aryl" may be used alone or as part of another word (e.g., in aryloxy, arylacyl). Preferred aryl have from six to about fourteen, preferably to about ten, carbon atoms in the aromatic ring(s), and a total of from about six to about twenty, preferably to about twelve, carbon atoms. Preferred aryl is phenyl or naphthyl; most preferred is phenyl (Ph). Preferred substituents of aryl include halo, alkyl, aryl, heterocycle, hydroxy, alkoxy, aryloxy, thio, alkylthio, arylthio, amino, alkylamino, arylamino, amide, alkylamide, arylamide, formyl, alkacyl, arylacyl, carboxy and its alkyl and aryl esters and amides, sulfo, alkylsulfo, arylsulfo, sulfino, alkylsulfino, arylsulfino, phospho, alkylphospho, arylphospho, phosphino, alkylphosphino, arylphosphino, nitro, and cyano. Substituents of aryl also include cycloalkyl and heterocyclic rings which are fused with the aryl ring or rings. Also unsubstituted aryl are preferred.

As used herein unless specified otherwise, "heterocycle" or "heterocyclic" means a saturated, unsaturated or aromatic cyclic hydrocarbon ring (or fused rings) with one or more heteroatoms in the hydrocarbon ring(s). Preferred heterocycles have from one to about six heteroatoms in the ring(s), more preferably one or two or three heteroatoms in the ring(s). Preferred heterocycles have from three to about fourteen, preferably to about ten, carbon plus heteroatoms in the ring(s), more preferably from three to about seven, more preferably still five or six, carbon plus heteroatoms in the rings(s); and a total of from three to about twenty carbon plus heteroatoms, more preferably from three to about ten, more preferably still five or six, carbon plus heteroatoms. Preferred heterocycles have one ring, but may have two, three, or more, fused rings. More preferred heterocyclic rings include those which are one ring with 5 or 6 carbon plus heteroatoms in the ring with no more than three ring heteroatoms, no more than two of which are 0 and S. Still more preferred are such 5- or 6-ring atom heterocycles with one or two ring atoms being 0 or S and the others being C; or with one, two or three ring atoms being N and the others being C. Such preferred 5- or 6-ring atom heterocycles are preferably saturated, unsaturated with one or two double bonds, or aromatic. Such preferred 5- or 6-ring atom heterocycles are preferably a single ring; or fused with a 3- to 6-ring atom hydrocarbon ring which is saturated, unsaturated with one double bond, or aromatic (phenyl); or fused with another such 5- or 6-rine atom heterocyclic ring. 1-heterocycles are unsubstituted or substituted. Preferred heterocycle substituents are the same as for alkyl.

As used herein, "strong base" means an inorganic hydroxide base, alkyl-alkali metal (e.g., n-butyl lithium), alkali metal hydride (e.g., sodium hydride), alkoxide salt (e.g., sodium methoxide), alkali metal amide (e.g., lithium diisopropyl amide), and the like. As used herein, "substantial amount" means a sufficient amount of a specified material such that it effects a subject invention process in a measurable way. As used herein, "substantially free" means a product or other material has less than about 10%, preferably less than about 5%, more preferably less than about 2%, more preferably still less than about 1% of the indicated compound.

As used herein, "non-protic and non-oxidizing solvent" means a solvent that does not dissociate to provide a substantial and measurable proton concentration, and does not have substantial oxidizing potential. Protic solvents include, for example, water, methanol, ethanol, dimethylformamide and the like. Oxidizing solvents include, for example, dimethylsulfoxide, and the like.

As used herein "combinatorial library" of compounds means a mixture of related compounds or a group of individual compounds, made substantially simultaneously by substantially the same process using a mixture of or individual related reactants to obtain related compounds. The combinational library may formed by reacting separate portions of the amino-substituted-TIQ-carboxylate with different $R^1$ and/or $R^2$-containing reactants. Alternatively, the combinatorial library may be formed by reacting amino-substituted-TIQ-carboxylate substrate with a mixture of $R^1$ containing reactants or a mixture of $R^2$-containing reactants. Finally, the combinatorial library may be formed by a method using a combination of these processes.

As used herein "protecting group" refers to a moiety attached to a functional group, such as an amine, to prevent an undesired reaction. Preferably the protecting group may be easily removed after protection of the functional group is no longer required. Suitable protecting groups include t-butyloxycarbonyl (Boc), 9-fluorenylmethoxycarbonyl (Fmoc), benzyloxycarbonyl, allyloxycarbonyl, and (trimethylsilyl)ethoxycarbonyl.

The present invention is directed to the synthesis of amino-substituted-TIQ-sulfonamide hydroxamic acids, particularly amino-substituted-TIQ-2-sulfonamide hydroxamic acids having the general structure:

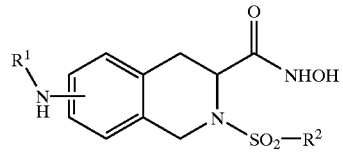

wherein $R^1$ and $R^2$ may be any desired moiety. Preferably $R^1$ is alkyl, aryl, a heterocyclic moiety, amide, sulfonamide, urea, thiourea, or alcohol, and $R^2$ is aryl, hetero-aromatic ring or hydrocarbocycle.

Synthetic methods in accordance with the present invention utilize a solid support for the synthesis of amino-tetrahydroisoquinoline-sulfonamide hydroxamic acids, preferably amino-substituted-tetrahydroisoquinoline-2-sulfonamide hydroxamic acids (amino-substituted-TIQ-2-sulfonamide hydroxamic acids). In one embodiment the solid support is a resin, preferably a polyester resin, a polyolefin resin such as polyethylene, or a polyvinyl resin such as polystyrene. As used herein, the term "polyester resins" is intended to include modified polyester resins.

Methods in accordance with the invention may comprise the steps of providing a support-bound amino-substituted-tetrahydroisoquinoline-carboxylate (amino-substituted-TIQ-carboxylate) wherein the ring nitrogen of the support-bound amino-substituted-TIQ-carboxylate has a protecting group; attaching a first moiety to the amino-substitutent group of the support-bound amino-substituted-TIQ-carboxylate; deprotecting the ring nitrogen by removal of the protecting group; reacting the ring nitrogen of the deprotected amino-substituted-TIQ-carboxylate with a sulfonyl chloride to form a support-bound intermediate; and cleaving the support-bound intermediate from the solid support to form the amino-substituted-TIQ-sulfonamide hydroxamic acid. The steps are performed at times and at temperatures sufficient for the desired reactions to occur.

The support-bound amino-substituted-TIQ-carboxylate may be formed in any suitable manner. For example, support-bound amino-substituted-carboxylate may be formed by providing a nitro-substituted-tetrahydroisoquinoline-carboxylic acid with a protecting group to form an orthogonally protected nitro-substituted-TIQ-carboxylic acid; attaching the orthogonally protected nitro-substituted-TIQ-carboxylic acid to the solid support, thereby forming carboxylate; and reducing the nitro group to form the orthogonally protected amino-substituted-TIQ-carboxylate. In another embodiment, tetrahydroisoquinoline-carboxylic acid is first bound to the support, and then nitrated in the 7-position, followed by reduction of the nitro group to an amino group.

The TIQ-carboxylate may be nitrated by any suitable manner, such as treatment with sulfuric acid and potassium nitrate or with nitronium tetrafluoroborate and acetonitrile. The nitro group may be reduced by any suitable manner, such as hydrogenation over a metal catalyst, preferably a palladium catalyst, $SnCl_2$ in dimethyl formamide or the like. The ring nitrogen may be protected and de-protected in any suitable manner. A suitable protection method comprises reacting the TIQ-carboxylate with di-t-butyl dicarbonate, 9-fluorenylmethyl, chloroformate (Fmoc-Cl), or 9-fluorenyl methoxyl carbonyl-N-hydroxy succinimide, while a suitable deprotection method comprises treatment with a strong acid such as trifluoroacetic acid or with an amine base such as piperidine. The protecting group may be selected from the group consisting of t-butyloxycarbonyl (Boc), 9-fluorenylmethoxycarbonyl (Fmoc), benzyloxycarbonyl, allyloxycarbonyl, (trimethylsilyl)ethoxycarbonyl and mixtures thereof.

Generally, the TIQ-carboxylate is attached to the solid support by any suitable manner. In one embodiment, the TIQ carboxylic acid is mixed with the solid support in dichloromethane in the presence of 4-dimethylamino pyridine and 1,3-diisopropyl-carbodiimide. In a preferred embodiment, the TIQ-carboxylate is attached to the solid support through the acid moiety, more particularly through reaction of the support with the hydroxyl segment of the carboxylic moiety to form a carboxylate.

In one embodiment, the invention is directed to methods of preparing an amino-substituted-tetrahydroisoquinoline-sulfonamide hydroxamic acid having the structure:

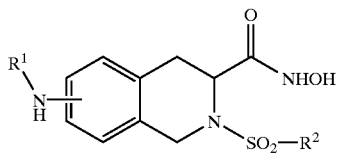

wherein $R^1$ is alkyl, aryl, heterocyclic moiety, amide, sulfonamide, urea, thiourea, or alcohol, and le is aryl, hetero-aromatic ring or hydrocarbocycle. The methods comprise the steps of: (a) providing an orthogonally protected amino-substituted-tetrahydroisoquinoline-carboxylate wherein the orthogonally protected amino-substituted-tetrahydroisoquinoline-carboxylate is attached to a solid support; (b) attaching an $R^1$ group to the amino substituent of the amino-substituted-tetrahydroisoquinoline-carboxylate; (c) removing the protecting group from the amino-substituted-tetrahydroisoquinoline-carboxylate; (d) reacting the deprotected, $R^1$-substituted amino-substituted-tetrahydroisoquinoline-carboxylate with a sulfonyl chloride having the structure $R^2SO_2Cl$ to form an intermediate attached to a solid support; and (e) cleaving the intermediate from the solid support to form an amino-substituted-tetrahydroisoquinoline-sulfonamnide hydroxamic acid.

While not being bound by theory, it is believed that amino-substituted-TIQ-2-sulfonamide hydroxamic acids in accordance with the invention are formed as set forth in Reaction Sequence 1 below, wherein $R^1$ is alkyl, aryl, heterocyclic moiety, amide, sulfonamide, urea, thiourea, or alcohol; $R^2$ is aryl, hetero-aromatic ring or hydrocarbocycle, and may comprise one or more substituents; W represents a support, such as a polystyrene resin; and Z represents a protecting group, such as t-butyloxycarbonyl (Boc), 9-fluorenylmethoxycarbonyl (Fmoc), benzyloxycarbonyl, allyloxycarbonyl, or 30 (trimethylsilyl)ethoxycarbonyl.

Reaction Sequence 1

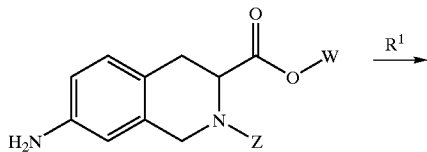

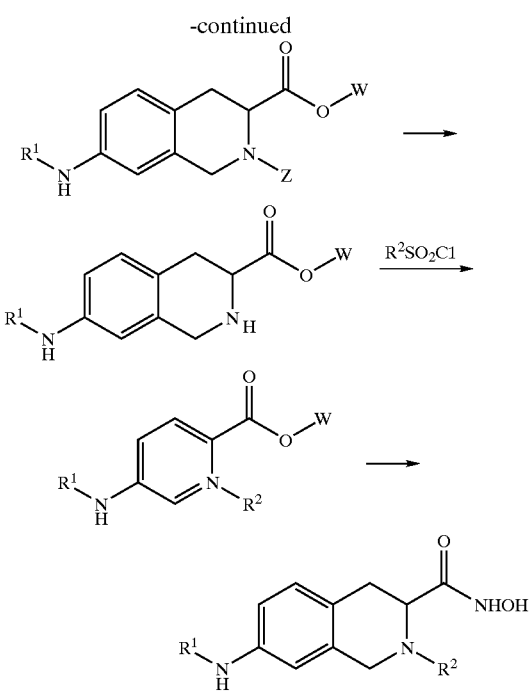

The step of attaching the $R^1$ group occurs at a temperature and for a time sufficient for the desired reaction to occur. Suitable $R^1$ groups include amides, sulfonamides, ureas, thioureas, alcohols, alkyls, aryls, heterocyclic moieties and mixtures thereof. Any desired moieties may be used to form the $R^1$ group, and suitable moieties include acyl halides, carboxylates, including amino acids; sulfonyl chlorides; isocyanates; isothiocyanates; epoxides; halides, including alkyl halides and aryl halides; aldehydes; and mixtures thereof. As used herein, "amino acids" is intended to include N-protected amino acids.

In one embodiment, the $R^1$ group is an amide formed by reacting the amino-substituted-TIQ-carboxylate resin with an acyl chloride, generally in the presence of N N-diisopropylethylamine (DIEPA) and dichloroethane. Preferably the reaction occurs at room temperature for a period of time of about 12 hours. In another embodiment the amide is formed by activating a carboxylic acid in solution using (benzotriazol-1-yloxy)-tris(pyrrolidino)phosphonium hexafluorophosphate (PyBOP) in dimethylformamide (DMF), and adding the solution to the amino-substituted-TIQ-carboxylic resin. Preferably the reaction occurs at room temperature for a period of time of from about 1 to about 2 hours. The carboxylic acid may be an amino acid, such as a N-protected amino acid.

In another embodiment, the $R^1$ group is a sulfonamide formed by reacting the amino-substituted-TIQ-carboxylate with a sulfonyl chloride, generally in the presence of 4-dimethylaminopyridine (DMAP) and pyridine. Preferably the step of forming the sulfonamide comprises reacting the in amino-substituted-TIQ-carboxylate with a sulfonyl chloride in the presence of about 1%, by weight, 4-dimethylaminopyrdine and pyridine at room temperature for from about 6 to about 12 hours. Generally the mole ratio of amino-substituted-TIQ-carboxylate to sulfonyl chloride is from about 1:2 to about 1:8, preferably from about 1:3 to about 1:5.

In another embodiment, the $R^1$ group is a urea or thiourea formed by reacting the amino-substituted-TIQ-carboxylate with an isocyanate or isothiocyanate. respectively, preferably the presence of NaH in dimethylformamide. Preferably the amino-substituted-TIQ-carboxylate is reacted with an isocyanate or isothiocyanate in the presence of about 1%, by weight NaH in dimethylformamide at room temperature for about 12 hours. Generally the mole ratio of amino-TIQ-carboxylate to isocyanate or isothiocyanate is from about 1:3 to about 1:5.

In another embodiment, the $R^1$ group is an alcohol formed by reacting the amino-substituted-TIQ-carboxylate with an epoxide in the presence of an alcohol solvent. Preferably the reaction occurs at a temperature of about 80° C. and for a time period of about 16 hours. In one embodiment the alcohol solvent is a mixture of ethanol and isopropanol, preferably in a volume ratio of about 1:1 ethanol:isopropanol. Generally the mole ratio of amino-TIQ-carboxylate to epoxide is from about 1:3 to about 1:5.

In another embodiment, the $R^1$ group is an alkyl formed by reacting the amino-substituted-TIQ-carboxylate with an alkyl halide, preferably an alkyl bromide. Generally the step of forming the aryl comprises reacting the amino-substituted-TIQ-carboxylate with an alkyl halide in the presence of $Bu_4NHSO_4$ and $Na_2CO_3$. In a preferred embodiment the step comprises reacting the amino-substituted-TIQ-carboxylate with an alkyl bromide in a solution comprising about 2%, by weight, $Bu_4NHSO_4$, about 5%, by weight, $Na_2CO_3$ and toluene at a temperature of about 70° C. for a period of time of about 8 hours. Generally the mole ratio of amino-substituted-TIQ-carboxylate to alkyl halide is from about 1:2 to about 1:4.

In another embodiment, the $R^1$ group is an alkyl formed by reductive alkylation. The amino-substituted-TIQ-carboxylate may be reacted with an aldehyde in the presence of a borane/pyridine complex. Preferably the step comprises reacting the amino-substituted-TIQ-carboxylate with an aldehyde in the presence of a borane/pyridine complex in a mixing component comprising ethanol and dimethyl formamide, more preferably the mixing solvent comprises ethanol and dimethyl formamide in a ethanol:dimethyl formamide weight ratio of about 3:1. Generally the mole ratio of amino-substituted-TIQ-carboxylate to aldehyde is from about 1:2 to about 1:4. The borane/pyridine complex is a commercially available reactant from Aldrich. A preferred $R^1$ group may be formed by reacting the amino-substituted-TIQ-carboxylate with benzoyl chloride in the presence of N,N-diisopropylethylamine or with benzaldehyde in the presence of a borane/pyridine complex.

Suitable $R^2$ groups include aryls, hetero-aromatic rings and hydrocarbocycles. The $R^2$ groups may comprise one or more substituents. In one embodiment, the $R^2$ group is an aryl comprising a substituent, a hetero-aromatic ring comprising a substituent, or a hydrocarbocycle, while in another embodiment, the $R^2$ group is an aryl comprising a substituent, a hetero-aromatic ring comprising a substituent, or a hydrocarbocycle comprising a substituent. Suitable substituents include alkyls, aryls, alkoxys, aryloxys, OH, alkylamines, arylamines, amides, esters, carboxylates, including amino acids, $NH_2$, acyls, $NO_2$, CN, amidines, hydroxyl-amidines, halides, alkylthios. arylthios, SH, and non-fused or fused 5-, 6- and 7-membered heterocycles. As used herein "amino acids" is intended to include N-protected amino acids.

The step of attaching the $R^2$ group occurs at a temperature and for a time sufficient for the desired reaction to occur. The $R^2$ group may be attached to the ring nitrogen by reacting amino-substituted-TIQ-carboxylate with a sulfonyl chloride having the structure $R^2SO_2Cl$. Generally the mole ratio of amino-substituted-TIQ-carboxylate sulfonyl chloride is from about 1:2 to about 1:8, preferably from about 1:3 to about 1:5. In one embodiment, the $R^2$ group is attached to the ring nitrogen of a support-bound amino-substituted-TIQ-carboxylate by reacting amino-substituted-TIQ-carboxylate with sulfonyl chloride, preferably in the presence of 4-dimethylaminopyridine and N,N-diisopropylethylamine. In a more preferred embodiment, the reaction occurs in the present of 1%, by weight, 4-dimethylaminopyridine (DMAP) and 1 equivalent of N,N-diisopropylethylamine (DIPEA) in dimethylformamide (DMF). The reaction may be performed at room temperature for a period of time of from about 6 to about 12 hours.

The support-bound intermediate may be cleaved to produce the substituted amino-substituted-TIQ-sulfonamide hydroxamic acid by any suitable manner. The cleavage step occurs at a temperature and for a time sufficient for cleavage to occur. A preferred cleavage step comprises treating the support-bound intermediate with a cleaving composition comprising $NH_2ONa$, $NH_2OH$ and methanol, preferably comprising $NH_2ONa$, $NH_2OH$, methanol, tetrahydrofuran and N,N-diisopropylethylamine. In one embodiment, the step of cleaving the intermediate from the solid support comprises treating the intermediate with the cleaving composition in a ratio of cleaving composition to solid support of about 1.5:1.

The cleaving composition may be prepared by mixing $NH_2OH-HCl$ with $NaOCH_3$ to form a first solution; and mixing the first solution with tetrahydrofuran and N,N-diisopropylethylamine. Generally about 1 equivalent of $NH_2OH-HCl$ is basified using about 1.5 equivalents of $NaOCH_3$. The $NaOCH_3$ is prepared from sodium and anhydrous methanol; the total volume of methanol used is calculated to form a 2 M concentration of $NH_2ONa$ in the resulting $NH_2ONa/NH_2OH$/methanol mixture. The $NH_2ONa/NH_2OH$/methanol mixture is then mixed with tetrahydrofuran and N,N-diisopropylethylamine in a weight ratio of about 1:10:0.5 to form the cleaving composition.

In a preferred embodiment, the cleaving step of the amino-substituted-TIQ-sulfonamide hydroxamic acid synthesis comprises the steps of agitating the intermediate attached to the solid support with the cleaving composition; obtaining a filtrate; treating the filtrate with an acidic ion exchange resin, such as DOWEX® resin; and evaporating the filtrate to obtain the amino-substituted-tetrahydroisoquinoline-sulfonamide hydroxamic acid. Preferably, the step of agitating the intermediate attached to the solid support with the cleaving composition is performed at room temperature for a period of time, for example from about 10 to about 100 minutes, preferably about 45 minutes.

If desired, the resulting substituted amino-substituted-TIQ-sulfonamide hydroxamic acid may be further isolated and/or purified by any art recognized method, such as solvent extraction and recrystallization, thin layer chromatography or high pressure liquid chromatography (HPLC).

The methods in accordance with the present invention may be conveniently used to form combinatorial libraries. In one embodiment, the invention is directed to the preparation of combinatorial libraries of amino-substituted-tetrahydroisoquinoline sulfonamide hydroxamic acids having the structure:

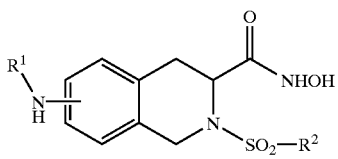

wherein $R^1$ and $R^2$ are as defined above. One method of preparing a combinatorial library of amino-substituted--TIQ-sulfonamide hydroxamic acids comprises the steps of: (a) providing a support-bound orthogonally protected amino-substituted--tetrahydroisoquinoline-carboxylate attached to a solid support; (b) attaching a first $R^1$ group to a first portion of support-bound orthogonally protected amino-substituted-tetrahydroisoquinoline-carboxylate and attach a second $R^1$ group to a second portion of support-bound orthogonally protected amino-substituted-tetrahydroisoquinoline-carboxylate; (c) deprotecting the first and second portions of support-bound orthogonally protected amino-substituted-tetrahydroisoquinoline-carboxylate to form first and second deprotected amino-substituted-tetrahydroisoquinoline-carboxylates; (d) attaching a first $R^2$ group to the ring nitrogen of the first deprotected amino-substituted-tetrahydroisoquinoline to form a first support-bound intermediate and attaching a second $R^2$ group to the ring nitrogen of the second deprotected amino-substituted-tetrahydroisoquinoline to form a second support-bound intermediate, and (e) cleaving the first and second support-bound intermediates from the solid support to form first and second amino-substituted-tetrahydroisoquinoline-sulfonamide hydroxamic acids.

When the first and second $R^1$ groups are the same then the first and second $R^2$ groups are different, and when the first and second $R^2$ groups are the same, then the first and second groups are different. Optionally, before step b, above, the orthogonally protected amino-substituted-tetrahydroisoquinoline-carboxylate may be partitioned into the first portion of orthogonally protected amino-substituted-tetrahydroisoquinoline-carboxylate and the second portion of orthogonally protected amino-substituted-tetrahydroisoquinoline-carboxylate.

Generally, the step of attaching the first and second $R^2$ groups to the first and second deprotected amino-substituted-tetrahydroisoquinoline-carboxylate, respectively, comprises reacting a first sulfonyl chloride with the ring nitrogen of the first deprotected amino-substituted-tetrahydroisoquinoline-carboxylate to form a first support-bound intermediate and reacting a second sulfonyl chloride with the ring nitrogen of the second deprotected amino-substituted-tetrahydroisoquinoline-carboxylate to form a second intermediate. The step of cleaving the support-bound intermediates from the solid support preferably comprises treating the support-bound intermediates with a cleaving composition, preferably a cleaving composition comprising $NH_2ONa$, $NH_2OH$, methanol, tetrahydrofuran and N,N-diisopropylethylamine.

EXAMPLE

An amino-substituted-TIQ-2-sulfonamide hydroxamic acid in accordance with the invention is prepared as set forth in Reaction Sequence 2, below, wherein W represents a support-BOC is t-butyloxycarbonyl; MeOH is methanol; THF is tetrahydrofuran; DIPEA is N,N-diisopropylethylamine; and DMAP is 4-(dimethylamino) pyridine.

Reaction Sequence 2.

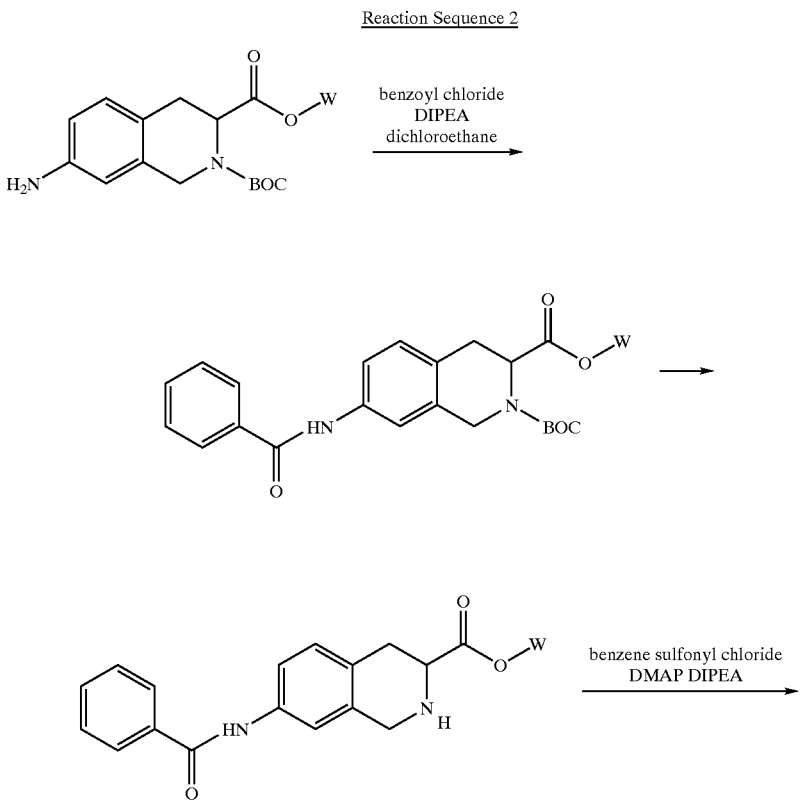

-continued

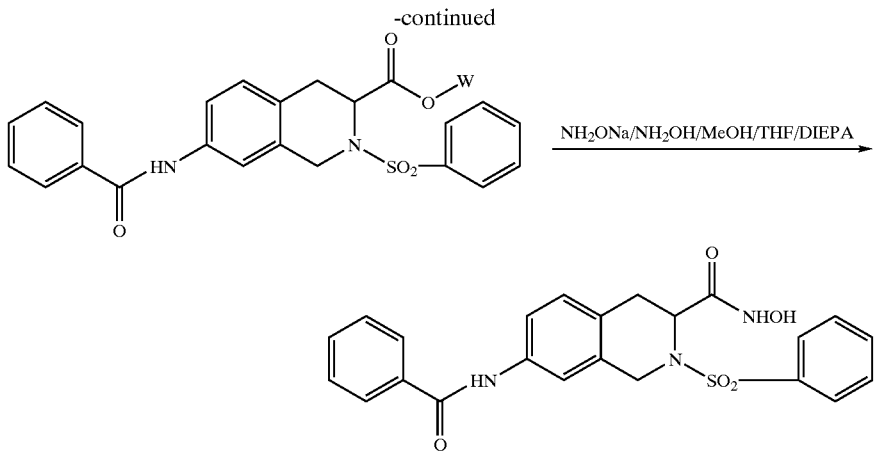

An orthogonally-protected (7-nitro-Boc-TIQ) carboxylate is prepared and attached to a solid support, such as a polyethylene resin. The 7-nitro group is reduced to a amino-substituted-group, and the support bound amino-substituted-TIQ-carboxylate is reacted with benzoyl chloride in the presence of N,N-diisopropylethylamine (DIEPA). After removal of the t-butyloxycarbonyl protecting group, the resulting support bound intermediate is treated with benzene sulfonyl chloride in the presence of DIPEA and DMAP. The product is cleaved from the support using a composition of NH$_2$ONa/NH$_2$OH/MeOH/THF/DIPEA.

Throughout the specification all percentages and ratios are by weight unless specifically indicated otherwise. Additional embodiments and modifications within the scope of the claimed invention will be apparent to one of ordinary skill in the art. Accordingly, the scope of the present invention shall be considered in the terms of the following claims, and is understood not to be limited to the details of the methods described in the specification.

What is claimed is:

1. A method of preparing an amino-substituted-tetrahydroisoquinoline-sulfonamide hydroxamic acid having the structure:

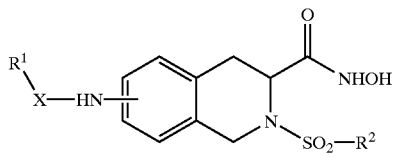

wherein R$^1$ is alkyl, aryl, heterocyclic moiety, or alcohol; X is selected from the group consisting of a bond, —CO—, —SO$_2$—, —NHCO—, and —NHCS—, and R$^2$ is aryl, hetero-aromatic ring or hydrocarbocycle, the method comprising the steps of: (a) providing an orthogonally protected amino-substituted-tetrahydroisoquinoline-carboxylate attached to a solid support; (b) attaching an R$^1$ group to the amino-substitutent of the orthogonally protected amino-substituted-tetrahydroisoquinoline-carboxylate; (c) removing a protecting group from the orthogonally protected amino-substituted-tetrahydroisoquinoline-carboxylate to form a deprotected, R$^1$-substituted amino-substituted-tetrahydroisoquinoline-carboxylate; (d) reacting the deprotected, R$^1$-substituted amino-tetrahydroisoquinoline-carboxylate with a sulfonyl chloride having the structure R$^2$SO$_2$Cl to form an intermediate attached to a solid support; and (e) cleaving the intermediate from the solid support to form an amino-substituted-tetrahydroisoquinoline-sulfonamide hydroxamic acid.

2. A method according to claim 1, wherein R$^2$ is a substituted aryl, a substituted hetero-aromatic ring, or a substituted hydrocarbocycle.

3. A method according to claim 1, wherein the step of reacting the deprotected R$^1$-substituted amino-substituted-tetrahydroisoquinoline-carboxylate with the sulfonyl chloride occurs in the presence of 4-dimethylaminopyridine and N,N-diisopropylethylamine.

4. A method according to claim 1, wherein the protecting group is t-butyloxycarbonyl.

5. A method according to claim 1, wherein the step of cleaving the intermediate from the solid support comprises treating the intermediate with a cleaving composition comprising NH$_2$ONa, NH$_2$OH and methanol.

6. A method according to claim 5, wherein the cleaving composition further comprises tetrahydrofuran and N,N-diisopropylethylamine.

7. A method according to claim 1, wherein the step of attaching the R$^1$ group comprises a step selected from the group consisting of: (i) reacting the orthogonally protected amino-substituted-tetrahydroisoquinoline-carboxylate with an acyl chloride in the presence of N,N-diisopropylethylamine and dichloroethane; (ii) activating a carboxylate in solution using (benzotriazol-1-yloxy)-tris (pyrrolidino)phosphonium hexafluorophosphate in dimethylformamide and adding the solution to the orthogonally protected amino-substituted-tetrahydroisoquinoline-carboxylate; (iii) activating a N-protected amino acid in solution using (benzotriazol-1-yloxy)-tris(pyrrolidino) phosphonium hexafluorophosphate in dimethylformamide and adding the solution to the orthogonally protected amino-substituted-tetrahydroisoquinoline-carboxylate; (iv) reacting the orthogonally protected amino-substituted-tetrahydroisoquinoline-carboxylate with a sulfonyl chloride in the presence of 4-dimethylaminopyridine and pyridine; (v) reacting the orthogonally protected amino-substituted-tetrahydroisoquinoline-carboxylate with an isocyanate in the presence of NaH in dimethylformamide; (vi) reacting the orthogonally protected amino-substituted-tetrahydroisoquinoline-carboxylate with an isothiocyanate in the presence of NaH in dimethylformamide; (vii) reacting the orthogonally protected amino-substituted-tetrahydroisoquinoline-carboxylate with an epoxide in the presence of an alcohol solvent; (viii) reacting the orthogonally protected amino-substituted-tetrahydroisoquinoline-carboxylate with an alkyl halide in the presence of Bu₄NHSO₄ and Na₂CO₃; and (ix) reacting the orthogonally protected amino-substituted-tetrahydroisoquinoline-carboxylate with an aldehyde in the presence of a borane/pyridine complex.

8. A method according to claim 1, wherein the solid support is a polystyrene resin.

9. A method according to claim 1, wherein the amino-substituted-tetrahydroisoquinoline-sulfonamide is 7-amino-tetrahydroisoquinoline-sulfonamide.

10. A method of preparing amino-substituted-tetrahydroisoquinoline-sulfonamide hydroxamic acid comprising the steps of: (a) providing an orthogonally protected amino-substituted-tetrahydroisoquinoline-carboxylate attached to a solid support; (b) attaching a moiety selected from the group consisting of amides, sulfonamides, ureas, thioureas, alcohols, alkyls and mixtures thereof to the amino-substitutent of the orthogonally protected amino-substitutent-tetrahydroisoquinoline-carboxylate; (c) removing a protecting group from the orthogonally protected amino-substituted-tetrahydroisoquinoline-carboxylate to obtain a deprotected amino-substituted-tetrahydroisoquinoline-carboxylate; (d) reacting the deprotected amino-substituted-tetrahydroisoquinoline-carboxylate with a sulfonyl chloride to form an intermediate attached to a solid support; and (e) cleaving the intermediate from the solid support to form an amino-substituted-tetrahydroisoquinoline-sulfonamide hydroxamic acid.

11. A method according to claim 10, wherein step a comprises:
(i) protecting the ring nitrogen of a 7-nitro-tetrahydroisoquinoline-carboxylic acid to form an orthogonally protected 7-nitro-tetrahydroisoquinoline-carboxylic acid; (ii) attaching the orthogonally protected 7-nitro-tetrahydroisoquinoline-carboxylic acid to a solid support, thereby forming a carboxylate; and (iii) converting the 7-nitro group to an amino group to form an orthogonally protected amino-substituted-tetrahydroisoquinoline-carboxylate.

12. A method according to claim 10, wherein the sulfonyl chloride has the structure R²SO₂Cl and R² is an aryl, a hetero-aromatic ring or a hydrocarbocycle.

13. A method according to claim 10, wherein the amino-substituted-tetrahydroisoquinoline-sulfonamide is 7-amino-tetrahydroisoquinoline-sulfonamide.

14. A method of preparing a combinatorial library of amino-substituted-tetrahydroisoquinoline sulfonamide hydroxamic acids having the structure:

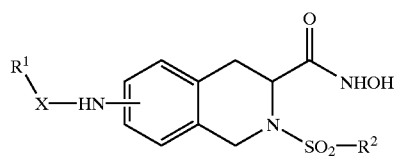

wherein R¹ is alkyl, aryl, heterocyclic moiety, or alcohol; X is selected from the group consisting of a bond, —CO—, —SO₂—, —NHCO—, and —NHCS—, and R² is aryl, hetero-aromatic ring or hydrocarbocycle, the method comprising the steps of: (a) providing an orthogonally protected amino-substituted-tetrahydroisoquinoline-carboxylate bound to a support; (b) attaching a first R¹ group to a first portion of the orthogonally protected amino-substituted-tetrahydroisoquinoline-carboxylate and attaching a second R¹ group to a second portion of the orthogonally protected amino-substituted-tetrahydroisoquinoline-carboxylate; (c) de-protecting the first and second portions of the orthogonally protected amino-substituted-tetrahydroisoquinoline-carboxylates to form first and second deprotected amino-substituted-tetrahydroisoquinoline-carboxylates; (d) attaching a first R² group to the ring nitrogen of the first deprotected amino-substituted-tetrahydroisoquinoline-carboxylate to form a first support-bound intermediate; and attaching a second R² group to the ring nitrogen of the second deprotected amino-substituted-tetrahydroisoquinoline-carboxylate form a second support-bound intermediate; and (e) cleaving the first and second support-bound intermediates from the solid support to form first and second amino-substituted-tetrahydroisoquinoline-sulfonamide hydroxamic acids; wherein, when the first and second R¹ groups are the same, the first and second R² groups are different, and wherein, when the first and second R² groups are the same, then the first and second R¹ groups are different.

15. A method according to claim 14, wherein step e comprises reacting a first sulfonyl chloride with the ring nitrogen of the first deprotected amino-substituted-tetrahydroisoquinoline to form the first intermediate and reacting a second sulfonyl chloride with the ring nitrogen of the second deprotected amino-substituted-tetrahydroisoquinoline to form the second intermediate.

16. A method according to claim 14, wherein the step of cleaving the intermediates from the solid support comprises treating the intermediates with a cleaving composition comprising NH₂ONa, NH₂OH, methanol, tetrahydrofuran and N,N-diisopropylethylamine.

17. A method according to claim 14, wherein the amino-substituted-tetrahydroisoquinoline-sulfonamide is 7-amino-tetrahydroisoquinoline-sulfonamide.

18. A method of preparing an amino-substituted-tetrahydroisoquinoline-sulfonamide hydroxamic acid comprising the steps of: (a) providing an amino-substituted-tetrahydroisoquinoline intermediate attached to a solid support and having the structure:

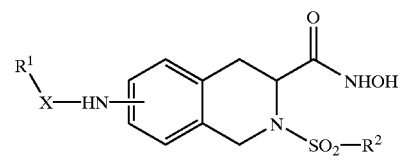

wherein R¹ is alkyl, aryl, heterocyclic moiety or alcohol, X is selected from the group consisting of a bond, —CO—, —SO₂—, —NHCO—, and —NHCS—, R² is aryl, hetero-aromatic ring or hydrocarbocycle; and W represents a solid support; and (b) cleaving the amino-substituted-tetrahydroisoquinoline intermediate from the solid support with a cleaving composition comprising NH₂ONa, NH₂OH and methanol to form an amino-substituted-tetrahydroisoquinoline-sulfonamide hydroxamic acid.

19. A method according to claim 18, wherein R² is a substituted aryl, a substituted hetero-aromatic ring, or a hydrocarbocycle.

20. A method according to claim 18, wherein the amino-substituted-tetrahydroisoquinoline-sulfonamide is 7-amino-tetrahydroisoquinoline-sulfonamide.

* * * * *

UNITED STATES PATENT AND TRADEMARK OFFICE
CERTIFICATE OF CORRECTION

PATENT NO. : 6,566,524 B2
DATED : May 20, 2003
INVENTOR(S) : Song Liu et al.

It is certified that error appears in the above-identified patent and that said Letters Patent is hereby corrected as shown below:

Column 10,
Lines 32 and 35, delete "$NH_2OH$-HCl" and insert -- $NH2OH \bullet HCl$ --.

Signed and Sealed this

Thirtieth Day of September, 2003

JAMES E. ROGAN
*Director of the United States Patent and Trademark Office*